United States Patent [19]
Park

[11] Patent Number: 5,874,123
[45] Date of Patent: Feb. 23, 1999

[54] PRECOATED POLYMERIC PROSTHESIS AND PROCESS FOR MAKING SAME

[76] Inventor: Joon B. Park, 1810 Country Club Dr., Coralville, Iowa 52241

[21] Appl. No.: 787,246

[22] Filed: Jan. 24, 1997

[51] Int. Cl.⁶ .................. B65D 3/10; B65D 1/38
[52] U.S. Cl. ............ 427/2.24; 427/412.3; 427/307; 427/322; 427/2.26
[58] Field of Search ................ 427/2.26, 412.3, 427/322, 307, 2.24

[56] References Cited

U.S. PATENT DOCUMENTS

| | | | |
|---|---|---|---|
| 3,713,860 | 1/1973 | Auskern | 427/2.26 |
| 4,164,794 | 8/1979 | Spector et al. | 427/195 |
| 4,213,816 | 7/1980 | Morris | 427/2.26 |
| 4,281,420 | 8/1981 | Raab | 427/2.26 |
| 4,454,612 | 6/1984 | McDaniel et al. | 427/2.26 |
| 4,491,987 | 1/1985 | Park . | |
| 4,554,686 | 11/1985 | Baker | 427/2.26 |
| 4,735,625 | 4/1988 | Davidson . | |
| 4,840,851 | 6/1989 | Golander et al. | 427/307 |
| 4,888,413 | 12/1989 | Domb | 528/272 |
| 5,035,714 | 7/1991 | Willert et al. . | |
| 5,061,286 | 10/1991 | Lyle | 623/16 |
| 5,346,495 | 9/1994 | Vargas, III | 606/92 |
| 5,529,736 | 6/1996 | Shalaby et al. . | |
| 5,593,719 | 1/1997 | Dearnaley et al. | 427/2.26 |

*Primary Examiner*—Diana Dudash
*Attorney, Agent, or Firm*—Dority & Manning, P.A.

[57] ABSTRACT

The present invention is directed to a polymeric prosthesis precoated with a bone cement compatible polymer. The bone cement compatible polymer coating, which can be polymethyl methacrylate, is bonded to the outer surface of the prosthesis. For instance, in one embodiment, the bone cement compatible polymer coating is believed to be copolymerized with the polymeric prosthesis. Once bonded to a polymeric prosthesis in accordance with the present invention, the precoat strengthens the interface between a bone cement and a prosthesis when the prosthesis is later implanted. The precoat also decreases the likelihood that the prosthesis will loosen and break away from the cement over time. The polymeric implant product of the present invention is particularly well suited for use as an acetabular cup or a tibia plateau in replacing hip joints and knee joints respectively.

26 Claims, 2 Drawing Sheets

PRECOATED POLYMERIC PROSTHESIS AND PROCESS FOR MAKING SAME

FIELD OF THE INVENTION

The present invention is generally directed to polymeric implant products. More particularly, the present invention is directed to a polymeric prosthesis for implantation into the body that has been precoated with a bone cement compatible polymer. The bone cement compatible polymer is added to improve the strength of the interface between the prosthesis and a bone cement once the prosthesis is implanted into the body. In general, the present invention is also directed to a process for coating a polymeric prosthesis with a bone cement compatible polymer.

BACKGROUND OF THE INVENTION

Prosthetic devices are artificial devices used to replace or strengthen a particular part of the body. Such devices can be used in humans or animals to repair or replace diseased or damaged bone, allied tissue associated with the bone, and/or joints associated with the bone. Primarily, prosthetic devices are used to correct or prevent skeletal deformities or injuries and to alleviate the pain and discomfort associated with the deformities or injuries.

When implanting a prosthesis, typically a receiving site or cavity is first prepared in an adjoining bone. In particular, the bone can be cut and reamed out in order to accommodate the prosthesis. A bone cement is then mixed and placed in the receiving site or cavity. A prosthesis is positioned in the bone cement, and the bone cement is subsequently cured and hardened affixing the prosthesis to the bone.

In most applications, bone cement is made from an acrylic polymeric material. Typically, the bone cement is comprised of two components: a dry power component and a liquid component, which are subsequently mixed together. The dry component generally includes an acrylic polymer, such as polymethyl methacrylate (PMMA). The dry component can also contain a polymerization initiator such as benzoyl peroxide, which initiates the free-radical polymerization process that occurs when the bone cement is formed.

The liquid component, on the other hand, generally contains a liquid monomer such as methyl methacrylate (MMA). The liquid component can also contain an accelerator such as an amine (e.g., N,N-dimethyl-p-toluidine). A stabilizer, such as hydroquinone, can also be added to the liquid component to prevent premature polymerization of the liquid monomer.

When the liquid component is mixed with the dry component, the dry component begins to dissolve or swell in the liquid monomer. The amine accelerator reacts with the initiator to form free radicals which begin to link monomer units to form polymer chains. In the next two to four minutes, the polymerization process proceeds changing the viscosity of the mixture from a syrup-like consistency (low viscosity) into a dough-like consistency (high viscosity). Ultimately, further polymerization and curing occur, causing the cement to harden and affix a prosthesis to a bone.

Once implanted, a prosthetic device ideally closely assimilates the characteristics of the bone and/or the joint that the device is intended to repair or replace. The implanted prosthetic device should be capable of supporting and withstanding stresses and strains normally imparted to the repaired or replaced bone joints.

The above process for implanting a prosthetic device is generally accepted within the art and has proven to be a successful process for repairing or replacing damaged bones, bone joints and the like. Prosthetic devices, however, can be prone to loosen within the bone cavity over time. In particular, the acrylic bone cement, which is neither as strong nor as viable as bone tissue, has been universally considered the weakest link in the implant design. It has been found that the bone cement can break away from the prosthesis, can break away from the bone, or can develop stress or fatigue cracks when repeatedly exposed to the normal stress and strains supported by the bones.

Due to these problems, attempts have been made to improve the mechanical properties of prosthetic devices and of the cement interface that exists between the device and the bone. For instance, U.S. Pat. No. 4,491,987, which was filed by the current inventor and which is incorporated herein in its entirety by reference, discloses an improved prosthesis and process for orthopedic implantation of the prosthesis. The current inventor's prior patent is generally directed to a prosthesis precoated with a polymeric material that is compatible with bone cement. Once implanted, the precoat provides a stronger interfacial bond between the bone cement and the prosthesis.

The present inventor's prior work provided great advances in the art with respect to the implantation of orthopedic devices, namely orthopedic devices made from metals such as stainless steel, titanium, and cobalt chrome alloys. However, although metallic devices have achieved relatively high degrees of success in repairing joints, these devices are not always well suited for every application. For instance, in some applications, it is preferred to use a more flexible and less rigid material than metal for opposing joint structures. Specifically, polymeric prosthetic devices are particularly well suited for use in replacing the acetabular cup in a hip replacement and replacing the tibia plateau in knee replacements.

Unfortunately, high strength polymeric materials, such as ultra high molecular weight polyethylene (UHMWPE), do not adhere well to conventional bone cement materials. Thus, in order to attach polymeric prosthetic devices to an adjoining bone using bone cement, deep grooves have been formed into the prosthetic devices for forming a mechanical interlock with the bone cement.

In other prior art constructions, polymeric prosthetic devices include a metal backing and stem for bonding the devices to a bone using a bone cement. Alternatively, the polymeric devices have been installed into a bone without cement using bone screws. Bony tissue ingrowth has also been proposed in the past as a means for joining a prosthesis to bone.

Thus far, however, these prior art methods and constructions for polymeric prosthetic devices have not proven to be completely successful. Thus, a need exists for a process for implanting a polymeric prosthesis into a prepared area of the body. More particularly, a need exists for a process that strengthens the interface between a bone cement and a polymeric prosthesis for decreasing the likelihood that the prosthesis will loosen and break away from the cement over time. Further, a need also exists for a precoated polymeric prosthesis that will readily adhere to a curing bone cement mixture once implanted into an adjoining bone.

SUMMARY OF THE INVENTION

The present invention provides further improvements in prior art constructions and methods.

Accordingly, it is an object of the present invention to provide a process for precoating a polymeric prosthesis with a bone cement compatible polymer.

It is another object of the present invention to provide an implant product including a polymeric prosthesis that has been precoated with a bone cement compatible polymer.

Another object of the present invention is to provide a process for bonding a bone cement compatible polymer coating to a polymeric prosthesis.

Still another object of the present invention is to provide an implant product that buffers the stress transfer from a prosthesis to a bone cement and to an adjoining bone by providing a gradual stiffness gradient from the surface of the prosthesis to the bone cement.

These and other objects of the present invention are achieved by providing a process for coating a polymeric prosthesis prior to being implanted into the body. The process includes the steps of providing a prothesis having a shape configured to be implanted into a prepared area of the body. The prosthesis includes a polymeric portion adapted to be attached to an adjoining bone with a bone cement. A coating of a bone cement compatible polymer is applied to the polymeric portion of the prosthesis. Specifically, it is believed that the coating of the bone cement compatible polymer is copolymerized with the polymeric portion of the prosthesis.

In one embodiment, the polymeric portion of the prosthesis is made from ultrahigh molecular weight polyethylene. Preferably, the bone cement compatible polymer coating applied to the prosthesis is up to about 2 mm thick, has a substantially pore free outer surface, and is made from an acrylic polymer. The acrylic polymer, in one embodiment, is polymethyl methacrylate.

The bone cement compatible polymer is bonded with the polymeric prosthesis by contacting the prosthesis with a solvent and a monomer. In particular, the solvent causes the monomer to bond to the polymeric prosthesis. Once pretreated with the solvent and the monomer, the prosthesis is then coated with a bone cement compatible polymer that polymerizes and bonds with the monomer bonded to the prosthesis.

The solvent used in the process of the present invention can be, for instance, xylene, chloroform, benzoin ethyl ether, or mixtures thereof. The solvent can be combined with the monomer in a ratio of from about 0.5:1 to about 2:1 by volume. The solvent and monomer can be heated to boiling and then contacted with the prosthesis. When using polymethyl methacrylate as the coating material, the monomer combined with the solvent can be methyl methacrylate.

After the prosthesis is pretreated with the solvent and monomer solution, preferably the solvent is substantially evaporated from the prosthesis. Further, after precoating the prosthesis with a bone cement compatible polymer, the polymeric prosthesis is annealed.

These and other objects of the present invention are also achieved by providing an implant product for implantation into the body. The implant product includes an underlying polymeric member having a shape configured to be implanted into a prepared area of the body. The polymeric member defines a surface adapted to be attached to an adjoining bone with a bone cement composition. A coating covers the surface of the polymeric member and is made from a bone cement compatible polymer. According to the present invention, the bone cement compatible polymer is believed to be chemically bonded, such as through copolymerization, with the polymeric member.

In one embodiment, the polymeric member is polyethylene and the bone cement compatible polymer is polymethyl methacrylate. As described above, the polymethyl methacrylate can be bonded to the polyethylene by contacting the polyethylene with a solvent and a liquid monomer that causes the liquid monomer to bond to the polyethylene. Thereafter the polyethylene is coated with a mixture of a polymethyl methacrylate which polymerizes and bonds to the monomer adhered to the polyethylene.

The implant product may be used to replace various bones and bone joints, and is particularly well suited for use as an acetabular cup or a tibia plateau.

Other objects, features and aspects of the present invention are discussed in greater detail below.

BRIEF DESCRIPTION OF THE DRAWINGS

A full and enabling disclosure of the present invention, including the best mode thereof, to one of ordinary skill in the art is set forth more particularly in the remainder of the specification, including reference to the accompanying figures in which.

Figure 1:
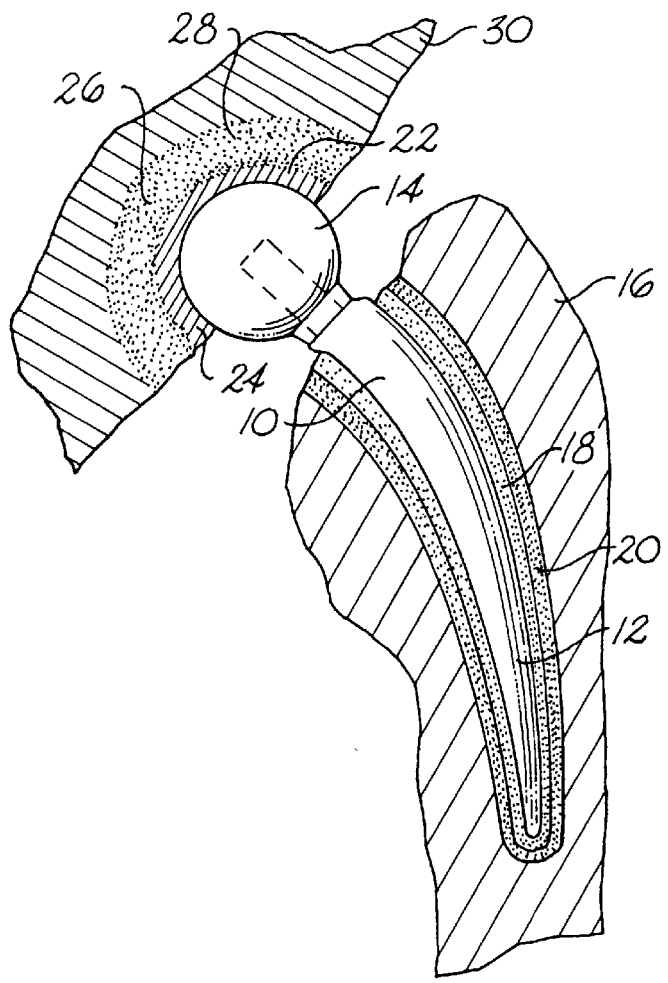
FIG. 1 is a partial cross-sectional view of a total hip implant, illustrating an embodiment of the present invention.

Repeat use of reference characters in the present specification and drawings is intended to represent same or analogous features or elements of the present invention.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction.

The present invention generally relates to the orthopedic implantation of polymeric prosthetic devices utilizing a bone cement as a fixative. More particularly, the present invention is directed to a process for precoating a prosthesis with a polymeric material that is compatible with the bone cement used during implantation. The coating provides a strong interfacial bond between the bone cement and the polymeric prosthesis, once the prosthesis is implanted into the body and attached to an adjoining bone.

Besides creating high interfacial strength between the polymeric prosthesis and the bone cement, the precoating improves and facilitates fixation of the implant to an adjoining bone by providing enhanced bonding with the bone cement. The precoating also provides a gradual stress transfer from the surface of the prosthesis to the surface of the adjoining bone due to the gradual change in stiffness from the polymer used to make the prosthesis, to the bone cement, and to the adjoining bone material. Further, by precoating the prosthesis, a lesser amount of bone cement is used during implantation, decreasing the degree of shrinkage the bone cement will undergo when cured and hardened. Ultimately, the precoating improves fixation of the implant and prevents loosening of the implant over time.

The process of the present invention is generally directed to bonding a coating of a bone cement compatible polymer to a polymeric prosthesis. It is believed that, through the process of the present invention, the bone cement compatible polymer coating is actually copolymerized with the structural polymer used to make the prosthesis. In one preferred embodiment, the prosthetic precoat is prepared from bone cement that is to be used during the operative implantation procedure. For instance, the prosthetic precoat can be made from polymethyl methacrylate (PMMA).

The prosthesis, on the other hand, can include a polymeric portion or can be entirely made from various polymeric materials. Such materials can include, for instance, polyolefins, such as polyethylene. In one preferred embodiment, the polymeric prosthesis that is bonded to the precoat is made from ultrahigh molecular weight polyethylene (UHMWPE). UHMWPE as defined herein has a molecular weight greater than $2 \times 10^6$ g/mole.

A detailed description of one embodiment of the process of the present invention will now be described. The following process is particularly well suited for precoating a polymeric prosthesis made from polyethylene with a polymethyl methacrylate coating. It should be understood, however, that various other polymeric materials can be used to construct the prosthesis and the precoating in accordance with the present invention.

In general, according to the process of the present invention, a polymeric prosthesis, such as made from polyethylene, is contacted with a pretreatment solution. The pretreatment solution contains a solvent and a monomer that, when polymerized, forms a bone cement compatible polymer. The solvent dissolves or swells an outer layer of the polymeric prosthesis which allows the monomer to infiltrate and bond with the prosthetic polymer. A precoat of a bone cement compatible polymer is then applied to the prosthesis. The coating of the bone cement compatible polymer polymerizes with the monomer bonded to the polymeric prosthesis. Ultimately, it is believed that a copolymer forms between the prosthetic polymer and the precoat made from the bone cement compatible polymer.

When the polymeric prosthesis is made from polyethylene, such as ultrahigh molecular weight polyethylene, the pretreatment solution can contain a xylene solvent. Polyethylene is highly stable to most chemicals and solvents, making it hard to react with other polymers. It has been found, however, that xylene is effective in dissolving or swelling the polyethylene for facilitating a reaction between the polyethylene and the liquid monomer contained in the pretreatment solution. Other solvents, however, may work equally as well as xylene. For instance, a chloroform solvent, a benzoin ethyl ether solvent, and mixtures of the various solvents may also be used.

When forming a precoating of polymethyl methacrylate on the polymeric prosthesis, preferably the monomer contained in the pretreatment solution is methyl methacrylate. The methyl methacrylate can be combined with the solvent in a volume ratio of from about 1:0.5 to about 1:2 respectively. Thus far, the best results have been obtained when the monomer to solvent ratio is approximately 1:1 by volume.

When using xylene as the solvent, preferably the pretreatment solution is heated prior to being contacted with the polymeric prosthesis. In particular, the solution should be heated to at least about the boiling point of xylene. For instance, at atmospheric pressure, the solution should be heated to about 100° C. to about 120° C.

The polymeric prosthesis can be contacted with the pretreatment solution by completely immersing the polymeric prosthesis in the solution. Alternatively, if only the portion of the prosthesis that is to be joined to a bone is to be precoated, then only a portion of the prosthesis is contacted with the pretreatment solution. The solvent may have a tendency to weaken the prosthesis. Thus, exposure to the pretreatment solution should be minimized.

In this regard, the length of time that the prosthesis is exposed to the pretreatment solution, for most applications, should be as short as possible in order to maintain the integrity of the prosthetic polymer. In general, the time of exposure to the pretreatment solution should be less than about three hours, and particularly less than about two hours. Although dependent upon the size of the prosthesis and upon the desired thickness of the precoating, in a preferred embodiment, the time of exposure is from about 40 minutes to about 2 hours.

Besides a solvent and a monomer, the pretreatment solution may contain other components. For instance, in one embodiment, the pretreatment solution may also contain small amounts of polymethyl methacrylate powder. When present, the polymethyl methacrylate may either bond with the monomer or directly to the polymeric prosthesis and facilitate attachment to the coating when later applied.

After the polymeric prosthesis has been contacted with the pretreatment solution, the prosthesis is then coated and bonded to a bone cement compatible polymer, such as polymethyl methacrylate. The polymeric precoat should be applied to substantially the entire surface of the prosthesis that is normally designed for immobilized fixation with an adjoining bone. Precoating of the prosthesis may be conducted in any suitable manner that will permit the attainment of a uniform coating over the surface of the prosthetic polymer. Preferably, the coating of the bone cement compatible polymer should be substantially completely polymerized for forming a pore free outer surface. By completely polymerizing the precoat, an improved interfacial bond between the prosthesis and the bone cement is achieved. If necessary, when the bone cement compatible polymer is applied to the prosthesis, the prosthesis can be subjected to temperatures and pressures that further promote polymerization of the precoat.

The bone cement compatible polymer is applied to the prosthesis while the bone cement compatible polymer is curing and hardening. In this manner, the bone cement compatible polymer polymerizes with and bonds to the monomer, which is attached to the prosthesis during exposure to the pretreatment solution. By polymerizing with the monomer, the bone cement compatible polymer is believed to form a copolymer with the polymer used to make the prosthesis. Thus, an enhanced bond forms between the polymeric prosthesis and the bone cement compatible polymer, ensuring that the precoat is firmly attached to the prosthesis.

The thickness of the bone cement compatible polymer coating will vary depending upon the size of the prosthesis and the particular location where the prosthesis is to be implanted. During implantation, adequate void space should be available between the precoated prosthesis and the bone cavity to enable fresh bone cement to totally surround the prosthesis. In most applications, the coating of the bone cement compatible polymer should be from about 0.1 mm to about 2 mm thick.

In one embodiment, when the monomer present in the pretreatment solution is methyl methacrylate, then the bone cement compatible polymer should be a corresponding acrylic polymer, such as polymethyl methacrylate. One commercially available polymethyl methacrylate polymer well suited for use in the present invention is DUZ ALL marketed by Coralite Dental Products which includes a polymethyl methacrylate powder that self-cures when mixed with a methyl methacrylate monomer liquid. When mixed and used in the process of the present invention as a precoat, the polymer powder and liquid monomer can be combined in a ratio (weight of polymer powder(g): volume of liquid monomer(ml)) of from about 1:2 to about 1:4. A polymerization initiator, such as benzoyl peroxide, can be present in the polymethyl methacrylate powder. An accelerator, such as N,N-dimethyl-p-toluidine can be present in the liquid monomer for facilitating polymerization of the polymethyl methacrylate polymer. When using a two component polymethyl methacrylate polymer as the precoating, the powder component is first mixed with the liquid monomer. After the two components have begun to react and polymerize, the mixture can be applied to the pretreated prosthesis and cured in forming the coating.

Preferably, after applying the precoating to the prosthesis or after the prosthesis has been pretreated, steps should be taken to ensure that the solvent contained in the pretreatment solution is completely evaporated from the implant product. For instance, when using xylene, the xylene can be evaporated from the prosthesis and from the precoating by placing the implant product in a vacuum oven for a time sufficient to remove the xylene.

As stated above, the solvent contained in the pretreatment solution may, in some circumstances, adversely affect the strength and mechanical properties of the polymeric prosthesis. Thus, in order to strengthen the prosthesis after being exposed to the pretreatment solution, the prosthesis after being precoated with the bone cement compatible polymer can be annealed at a suitable temperature and pressure. For instance, the precoated prosthesis can be placed in a heated and pressurized mold for a time sufficient for the prosthetic polymer to regain its original physical properties. For example, in one embodiment, the precoated prosthesis can be placed in a vacuum oven at a temperature of less than 100° C. and at a pressure of about 1,000 psi.

According to the present invention, once a first precoating of the bone cement compatible polymer is placed on the prosthesis, further polymeric coatings may be subsequently applied if desired. For instance, further layers of the bone cement compatible polymer can be applied to the prosthesis in order to increase the overall thickness of the precoat. Also, various layers of different polymeric materials can be applied to the surface of the prosthesis in order either to facilitate later bonding with a bone cement or to provide the precoated implant product with desired mechanical properties.

Once the polymeric prosthesis has been precoated according to the process of the present invention, the resulting implant product can be implanted into the body as desired. When the implant product is implanted, first, a receiving site is prepared in an adjoining bone. The two components of the bone cement are then mixed and kneaded until a doughy consistency is obtained. A mixing-kneading time of about four minutes is recommended. The doughy cement is forced into the bone cavity with enough force and pressure to place the cement in the prepared bone bed.

The precoated prosthesis can be wiped with a liquid monomer prior to being inserted into the receiving site. It is believed that wiping the implant product with the liquid monomer will dissolve some of the surface of the bone cement compatible polymer coating and thus foster a good interfacial bond between the precoat and the bone cement contained in the receiving site. Once the precoated prosthesis is placed in the receiving site, the bone cement is cured and hardened.

Once the implant product of the present invention is implanted into the body, the bone cement compatible polymer coating provides a shock gradient that assists in distributing the loads placed on the implanted bone. More particularly, the precoat buffers the stress transfer from the prosthesis to the bone cement and ultimately from the bone cement to the bone by providing a gradient of stiffness from the surface of the prosthesis to the bone cement. According to the present invention, it is believed that copolymerization between the polymeric prosthesis and the bone cement compatible polymer occurs within an interfacial layer of the implant, between the prosthesis and the bone cement compatible polymer coating. Within this layer, the concentration of the bone cement compatible polymer gradually increases for providing a stiffness gradient.

By carefully controlling the conditions at which bonding occurs between the polymeric prosthesis and the bone cement compatible polymer, the stiffness gradient occurring in the outer layer of the prosthesis can be carefully controlled as desired. Specifically, implant products with different stiffness gradients may be preferred depending upon the placement of the prosthesis and various other factors. Besides varying the copolymerization conditions, the stiffness gradient can also be altered and modified by blending different polymeric materials together in forming the precoat of the present invention. In one embodiment, the entire polymeric prosthesis itself can be made from blending or copolymerizing the prosthetic polymer with one or more bone cement compatible polymers.

By providing a stiffness gradient between the prosthesis and the bone cement, the precoat of the present invention not only strengthens the bond between the prosthesis and the bone cement but also serves to prevent loosening of the implant over time.

Although capable of being used in any suitable application, the polymeric implant product of the present invention is particularly well suited for load bearing joint implants, such as the acetabular cup of a total hip implant, a tibia plateau of a knee joint or the cup in a shoulder replacement. Referring to FIG. 1, a total hip implant is illustrated. The hip implant includes a hip prosthesis 10 having a stem 12 and a head 14. Hip prosthesis 10, although capable of being made from a polymeric material according to the present invention, is more commonly made from a metallic material. As shown, hip prosthesis 10 has been inserted into a cavity defined by a bone 16, such as a femur.

When hip prosthesis 10 is constructed from a metallic material, the prosthesis can include a polymer precoat 18 which strengthens the bond between stem 12 and a bone cement 20.

The hip implant illustrated in FIG. 1 further includes a precoated polymeric acetabular cup 22 made in accordance with the present invention. Acetabular cup 22 is more particularly illustrated in FIGS. 2 and 3. As shown in FIG. 1, acetabular cup 22 is adapted to receive head 14 of hip prosthesis 10.

Figure 2:
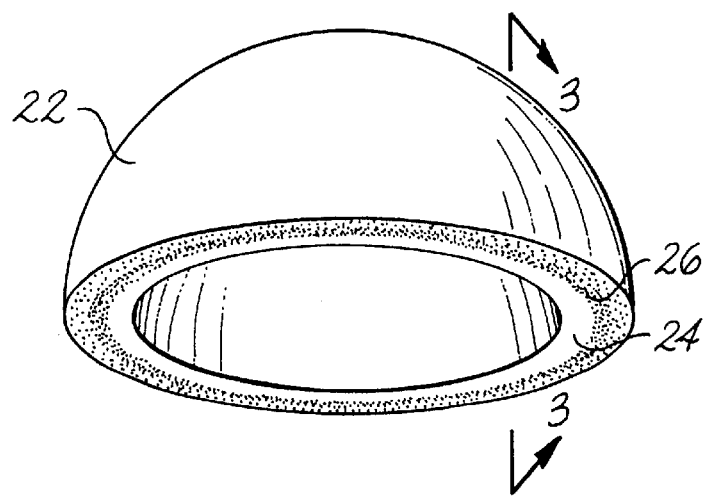
FIG. 2 is a perspective view of one embodiment of a precoated polymeric prosthesis made in accordance with the present invention.
Figure 3:
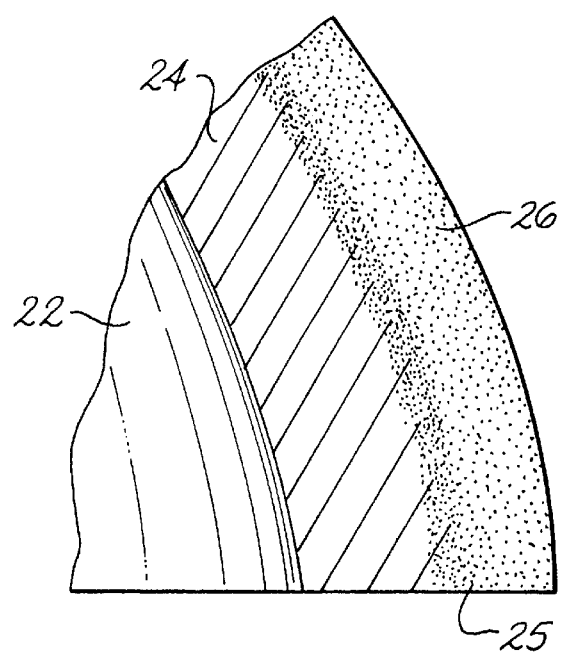
FIG. 3 is a partial cross-sectional view taken along line 3—3 of FIG. 2.

Acetabular cup 22 is made from an underlying polymeric portion 24 bonded to a bone cement compatible polymer coating 26 as more clearly shown in FIGS. 2 and 3. Coating 26 is bonded, such as through copolymerization, to polymeric portion 24. As shown in FIG. 1, bone cement compatible coating 26 is in turn bonded to a bone cement 28 which affixes acetabular cup 22 to a hip bone 30.

As described above, bone cement compatible polymer coating 26 can be applied to polymeric portion 24 to form a stiffness gradient for buffering stress transfer from acetabular cup 22 to bone cement 28. As shown in FIG. 3, acetabular cup 22 includes an interfacial layer 25 between polymeric portion 24 and bone cement compatible polymer coating 26. Interfacial layer 25 represents the area in which coating 26 is bonded to polymeric portion 24. More particularly, across interfacial layer 25 towards coating 26, there is a gradual increase in the concentration of the bone cement compatible polymer and there is a gradual decrease in the concentration of the polymer used to construct polymeric portion 24. This concentration gradient translates into a stiffness gradient as described above.

Figure 4:
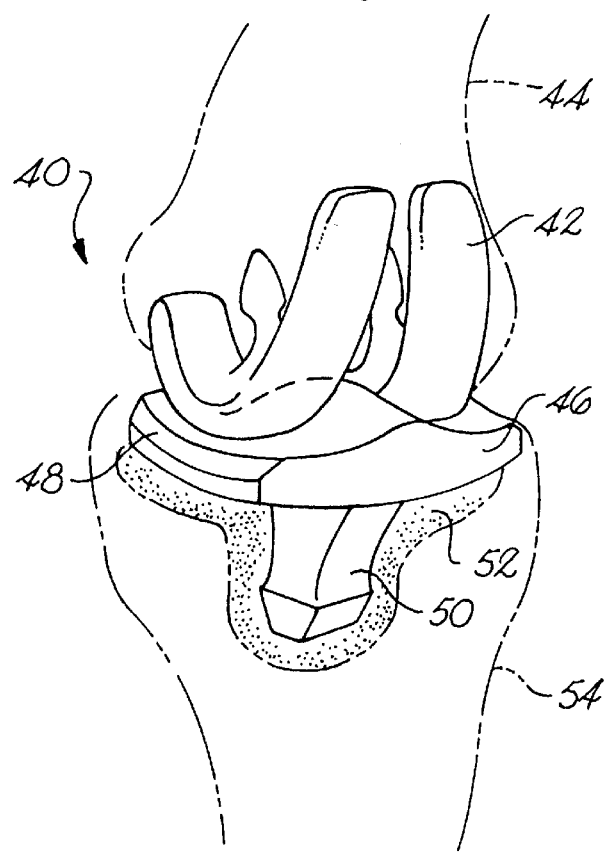
FIG. 4 is a perspective view of a knee implant, illustrating another embodiment of the present invention.

Besides an acetabular cup, a polymeric implant made according to the present invention is also particularly well suited for use as a tibia plateau in a knee replacement as illustrated in FIG. 4. As shown, knee replacement generally 40 includes a condylar implant 42 attached to a femur bone 44. In most applications, condylar implant 42 is made from a metal and is secured to femur 44 by screws or through the use of a bone cement.

Adjoining condylar implant 42 in FIG. 4 is a tibia plateau 46 made in accordance with the present invention. Tibia plateau 46 includes a top portion 48 and a stem portion 50. In one preferred embodiment, tibia plateau 46 is made from ultra high molecular weight polyethylene. At least stem portion 50 and the bottom of top portion 48 of tibia plateau 46 are precoated and copolymerized with a bone cement compatible polymer, such as polymethyl methacrylate. The precoating is subsequently bonded to bone cement 52 when implanted into a tibia 54. The precoating provides higher interfacial strength between the polyethylene polymer and the bone cement, thereby preventing loosening of the implant over time.

The present invention may be better understood with reference to the following examples.

EXAMPLE NO. 1

The following tests were performed in order to calculate the diffusion constant for pure xylene in ultra high molecular weight polyethylene.

Four (4) different sized samples made from UHMWPE were immersed in xylene at boiling temperature (approximately 129° C.). When placed in the xylene, the polymer samples began to swell. The weight of each sample over time was monitored until maximum weight gain was observed. From the amount of xylene absorbed by the polymer samples over time, a flux measurement and a concentration gradient measurement were calculated. The following results were obtained:

TABLE 1

Measurements of xylene diffusion into UHMWPE

| Sample Dimension (mm) | Amount of Xylene Absorbed (g) | Time of Complete Swelling (min) | Flux (g/cm²min) | Concentration Gradient (g/cm⁴) |
|---|---|---|---|---|
| 11 × 11 × 11 | 1.257 | 12 | 0.0144 | 1.72 |
| 16 × 16 × 16 | 2.9215 | 28 | 0.0068 | 0.89 |
| 21 × 21 × 21 | 7.6815 | 47 | 0.0062 | 0.79 |
| 26 × 26 × 26 | 16.1973 | 73 | 0.0055 | 0.71 |

The diffusion constant (D) from Fick's First Law was calculated from the following equation: $J(flux) = D (dc/dx)$.

From the data in Table 2, the diffusion constant was calculated to equal 0.009 cm²/min. Pretreatment solutions containing xylene in combination with a liquid monomer, however, may result in higher diffusion constants, since they have been discovered to diffuse faster.

By calculating the diffusion constant for a particular pretreatment solution, the amount of liquid monomer that is allowed to diffuse into the polymeric prosthesis may be controlled. In this manner, the amount of bonding that occurs between the bone cement compatible coating and the underlying polymeric member can be calculated, adjusted and varied as desired.

EXAMPLE NO. 2

The following tests were conducted in order to demonstrate that copolymerization occurs beneath the surface of the polymeric prosthesis.

Two (2) UHMWPE samples (½"×¼"×2") were immersed in a solution containing xylene and methyl methacrylate in a one to one volume ratio at 116° C. One sample was placed in the solution for one hour, while the second sample was placed in the solution for two hours.

A coating of polymethyl methacrylate (obtained from Aldrich Chemical Co. in Milwaukee, Wis.) was then applied and bonded to each sample. Specifically, polymethyl methacrylate powder was mixed with methyl methacrylate monomer in a 1 to 2 weight to volume ratio and applied to the samples.

Each sample was sliced several times from a selected surface. Oxygen content at the newly exposed surface was then measured using Electron Spectroscopy for Chemical Analysis (ESCA). Oxygen content indicates the presence of polymethyl methacrylate, since polymethyl methacrylate contains oxygen but UHMWPE does not. The following results were obtained:

TABLE 2

Normalized oxygen content from ESCA analysis on the pre-coated specimens

| Treatment (xylene to MMA volume ratio and time) | Depth from Surface (mm) | Normalized O₂ Content |
|---|---|---|
| 1:1, 1hr | 0.58 | 0.41 |
|  | 1.49 | 0.12 |
|  | 1.82 | 0.2 |
|  | 2.25 | 0.15 |
| 1:1, 2hr | 0.43 | 0.39 |
|  | 0.91 | 0.098 |
|  | 1.31 | 0.082 |
|  | 1.77 | 0.228 |

The above results demonstrate that the amount of polymethyl methacrylate inside the UHMWPE is diffusion controlled and that the penetration depth profile appears the be logarithmic.

Scanning electron microscopic pictures were taken of the samples as they were sliced. The pictures showed disruptions in the UHMWPE matrix caused by the xylene cleaving the polyethylene chains to form what appeared to be chemical bonds between the polyethylene and the polymethyl methacrylate.

EXAMPLE NO. 3

The following tests were conducted in order to determine the affect of pretreatment conditions on the interfacial strength between a coating of polymethyl methacrylate and a UHMWPE specimen.

UHMWPE samples (½"×¼"×2") were immersed in various solutions of xylene and methyl methacrylate at different volumetric ratios for different lengths of time. The temperature of the pretreatment solution was kept constant at 115° C. After being pretreated, the samples were coated with polymethyl methacrylate. The polymethyl methacrylate was obtained from Aldrich Chemical Co. in Milwaukee, Wis. In forming the polymethyl methacrylate, a polymethyl methacrylate powder was combined with a methyl methacrylate monomer in a 1 to 2 weight to volume ratio. The polymethyl methacrylate coating bonded to the underlying polyethylene specimen.

One end of each coated sample was bonded to bone cement using a mold. The samples were placed in a materials testing machine (MTS Model 810) which measured the tensile strength of the bond between the UHMWPE and the bone cement. Specifically, a constant cross-head speed of 0.1 mm/sec was applied to each sample until failure occurred. The following results were obtained:

TABLE 3

Pretreatment variations on the UHMWPE and results of interfacial tensile strength (ITS) measurements

| Volumetric Ratio of Xylene to MMA | Time (hr) | ITS (MPa) |
| --- | --- | --- |
| 2:3 | 1 | 9.45 |
| 2:3 | 2 | 9.99 |
| 2:3 | 3 | 7.41 |
| 2:3 | 3.5 | 7.13 |
| 1:1 | 1 | 11.38 |
| 1:1 | 2 | 8.33 |
| 3:2 | 1 | 4.96 |

As shown above, the best result was obtained when the ratio of xylene to MMA was 1 to 1 and the sample was exposed to the solution for 1 hour.

EXAMPLE NO. 4

Further precoated samples were made according to the process described in Example 3. For each sample, the pretreatment solution contained xylene and methyl methacrylate in a one to one volume ratio. The pretreatment time was varied between ten minutes and fifty minutes. After pretreatment, the samples were coated with a polymethyl methacrylate composition. The polymethyl methacrylate composition was made by combining polymethyl methacrylate powder with methyl methacrylate in a one to two or in a 1 to 4 weight to volume ratio.

Once precoated, the samples were bonded to bone cement using a mold. The tensile strength of the polyethylene-bone cement interface was then measured. The following results were obtained:

TABLE 4

Summary of the interfacial tensile strength (ITS) tests for varying treatment time for 1:1 (X:M) ratio pretreated specimens

| Pretreatment time | ITS (MPa) |
| --- | --- |
| 10 min | 5.33 |
| 20 min | 8.67 |
| 30 min | 8.73 |
| 40 min | 11.21 |

TABLE 4-continued

Summary of the interfacial tensile strength (ITS) tests for varying treatment time for 1:1 (X:M) ratio pretreated specimens

| Pretreatment time | ITS (MPa) |
| --- | --- |
| 40 min[a] | 12.01 |
| 50 min | 13.06 |

[a]pre-coating solution is made of 1:4 PMMA:MMA ratio instead of 1:2 for all others.

For each pretreatment time listed above, six samples were fabricated and tested. The results were averaged.

As shown above, the interfacial tensile strength increased as the pretreatment time increased. It was also noted that the forty minute pretreatment sample coated with a polymethyl methacrylate composition made from polymethyl methacrylate powder combined with methyl methacrylate in a one to four ratio were stronger than the samples coated with polymethyl methacrylate powder and methyl methacrylate in a one to two ratio. It is believed that the one to four ratio polymethyl methacrylate composition provided a more uniform flow on the surface of the specimen due to its lower viscosity.

EXAMPLE NO. 5

Besides varying the pretreatment conditions, the coating composition was also varied to determine its affect on tensile strength.

A number of UHMWPE samples were pretreated and coated with polymethyl methacrylate as described in Example 3 above. Specifically, the pretreatment solution for each sample contained xylene and methyl methacrylate in a volumetric ratio of 1 to 1. The samples were subjected to the pretreatment solution for 60 minutes at 115° C.

After pretreatment, the samples were coated with a polymethyl methacrylate composition. The amount of polymethyl methacrylate powder in relation to the amount of methyl methacrylate monomer was varied for each sample. Also, the amount of accelerator (N,N-dimethyl-p-toluidine) and the amount of initiator (dibenzoyl peroxide) were varied. Further, ultraviolet light was used to cure some of the polymethyl methacrylate coatings.

After the samples were coated with polymethyl methacrylate, one surface of each sample was bonded to a polymethyl methacrylate bone cement. Tensile strength tests were then conducted as described above. The following results were obtained:

TABLE 5

Results of varying pre-coating conditions and interfacial tensile strength (ITS)

| Group | PMMA:MMA Ratio | Initiator, Accelerator | UV Light | ITS (MPa) |
| --- | --- | --- | --- | --- |
| 1 | 1:4 | 1 | N | 5.53 |
| 2 | 1:4 | 2 | N | 9.08 |
| 3 | 1:2 | 1 | N | 12.52 |
| 4 | 1:2 | 2 | N | 9.52 |
| 5 | 1:4 | 1 | Y | 9.37 |
| 6 | 1:4 | 2 | Y | 9.71 |
| 7 | 1:2 | 1 | Y | 7.20 |
| 8 | 1:2 | 2 | Y | 8.69 |

For each group above four specimens were tested and the results were averaged.

As shown above, the best result was obtained by Group 3, in which the polymethyl methacrylate powder to methyl methacrylate monomer weight to volume ratio was 1 to 2. Apparently, UV light had no noticeable affect on tensile strength. The results also show that doubling the amount of initiator and accelerator generally increased the interfacial tensile strength.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A process for coating a polymeric prosthesis, said process comprising the steps of:
   providing a prosthesis having a shape configured to be implanted into a prepared area of the body, said prosthesis including a polymeric member, said polymeric member being adapted to be attached to an adjoining bone with a bone cement;
   contacting said polymeric member with a pretreatment solution comprising a solvent and a monomer, said solvent causing said polymeric member to swell and bond to said monomer; and
   applying a coating of a bone cement compatible polymer to at least a portion of said polymeric member of said prosthesis, said bone cement compatible polymer polymerizing with said monomer bonded to said polymeric member causing said bone cement compatible polymer to adhere to said polymeric member.

2. A process as defined in claim 1, wherein said polymeric member comprises ultrahigh molecular weight polyethylene.

3. A process as defined in claim 1, wherein said coating of said bone cement compatible polymer is up to about 2 millimeters thick.

4. A process as defined in claim 1, wherein said coating of said bone cement compatible polymer has a substantially pore free outer surface.

5. A process as defined in claim 1, wherein said bone cement compatible polymer comprises an acrylic polymer.

6. A process as defined in claim 1, wherein said bone cement compatible polymer comprises polymethyl methacrylate.

7. A process as defined in claim 1, wherein said prosthesis is made entirely of a polymer.

8. A process as defined in claim 1, wherein said coating of said bone cement compatible polymer copolymerizes with said polymeric member of said prosthesis.

9. A process as defined in claim 1, wherein said solvent comprises xylene, said xylene and said monomer being combined in a ratio of from about 0.5:1 to about 2:1 by volume.

10. A process as defined in claim 1, wherein said solvent comprises a material selected from the group consisting of xylene, chloroform, benzoin ethyl ether and mixtures thereof.

11. A process as defined in claim 1, further comprising the step of drying said polymeric member prior to applying said coating of said bone cement compatible polymer.

12. A process as defined in claim 1, wherein said pretreatment solution is heated to a temperature at about the boiling point of said solvent when contacted with said polymeric member.

13. A process as defined in claim 12, wherein said solvent comprises xylene, and wherein said pretreatment solution is heated to a temperature of from about 100° C. to about 120° C.

14. A process as defined in claim 1, wherein said monomer contained in said pretreatment solution comprises methyl methacrylate.

15. A process as defined in claim 14, wherein said pretreatment solution further comprises polymethyl methacrylate.

16. A process as defined in claim 1, further comprising the step of annealing said prothesis after applying said coating of said bone cement compatible polymer in a manner so as to evaporate substantially all of said solvent that may remain within said prothesis.

17. A process for coating a polymeric prosthesis with a bone cement compatible polymer for improving the bond between said prosthesis and a bone cement, said process comprising the steps of:
   providing a prosthesis made from a polymer;
   contacting said prosthesis with a solvent and a monomer, said solvent causing said monomer to bond with said polymer; and
   coating said prosthesis with a composition comprising a bone cement compatible polymer, said bone cement compatible polymer polymerizing and bonding with said monomer bonded to said polymer for adhering said bone cement compatible polymer to said prosthesis.

18. A process as defined in claim 17, wherein said prosthesis is made from a polymer comprising polyethylene.

19. A process as defined in claim 18, wherein said solvent comprises a material selected from the group consisting of xylene, chloroform, benzoin ethyl ether, and mixtures thereof.

20. A process as defined in claim 19, wherein said solvent and said monomer are present in a ratio of from about 0.5:1 to about 2:1 by volume when contacting said prosthesis.

21. A process as defined in claim 17, wherein said prosthesis is contacted with said solvent and said monomer at a temperature sufficient to boil said solvent.

22. A process as defined in claim 17, wherein said prosthesis is contacted with said solvent and said monomer for up to about 1 hour.

23. A process as defined in claim 17, further comprising the step of evaporating said solvent from said prosthesis after said prosthesis has been contacted with said solvent and said monomer.

24. A process as defined in claim 17, further comprising the step of annealing said polymeric prosthesis after being coated with said bone cement compatible polymer.

25. A process as defined in claim 19, wherein said monomer comprises methyl methacrylate and said bone cement compatible polymer comprises polymethyl methacrylate.

26. A process as defined in claim 25, wherein said solvent comprises xylene.

* * * * *